US009333157B2

(12) United States Patent
Jiang et al.

(10) Patent No.: US 9,333,157 B2
(45) Date of Patent: May 10, 2016

(54) BAR SOAP COMPOSITIONS CONTAINING ZINC PYRITHIONE AND A METAL-PYRIDINE OXIDE COMPLEX

(71) Applicant: The Procter & Gamble Company, Cincinnati, OH (US)

(72) Inventors: Chunpeng Jiang, Beijing (CN); Brian Joseph Limberg, Milford, OH (US); Edward Dewey Smith, III, Mason, OH (US); Juan Wang, Beijing (CN); Zhe Liu, Beijing (CN); Enjun Cheng, Beijing (CN); Casey Patrick Kelly, Wyoming, OH (US); Jason Edward Cook, Cincinnati, OH (US); Patrick Christopher Stenger, Fairfield, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 14/208,821

(22) Filed: Mar. 13, 2014

(65) Prior Publication Data
US 2014/0274852 A1 Sep. 18, 2014

(30) Foreign Application Priority Data

Mar. 14, 2013 (WO) ................ PCT/CN2013/072648
Feb. 26, 2014 (WO) ................ PCT/CN2014/072565

(51) Int. Cl.
*A61Q 19/10* (2006.01)
*A61K 8/02* (2006.01)
*A61K 8/58* (2006.01)
*C11D 10/04* (2006.01)
*A61Q 17/00* (2006.01)
(Continued)

(52) U.S. Cl.
CPC ... *A61K 8/58* (2013.01); *A61K 8/27* (2013.01); *A61K 8/361* (2013.01); *A61K 8/37* (2013.01); *A61K 8/4926* (2013.01); *A61K 8/4933* (2013.01); *A61Q 17/005* (2013.01); *A61Q 19/10* (2013.01); *C11D 3/168* (2013.01); *C11D 10/04* (2013.01); *A61K 2800/58* (2013.01); *A61K 2800/805* (2013.01); *C11D 1/04* (2013.01)

(58) Field of Classification Search
CPC ..... A61K 8/4933; A61K 8/58; A61K 8/0216; A61Q 17/005; A61Q 19/10
See application file for complete search history.

(56) References Cited

U.S. PATENT DOCUMENTS 2,809,971 A 10/1957 Bernstein et al.
3,235,455 A 2/1966 Judge et al.
(Continued)

FOREIGN PATENT DOCUMENTS

DE 10 2008 062 771 A1 7/2010
EP 0034385 A2 8/1981
EP 0093541 A2 11/1983
(Continued)

OTHER PUBLICATIONS

U.S. Appl. No. 13/856,457, filed May 22, 2013, Cook et al.
U.S. Appl. No. 14/255,714, filed Apr. 17, 2014, Jiang et al.
U.S. Appl. No. 13/890,369, filed May 9, 2013, Smith III et al.
(Continued)

*Primary Examiner* — Necholus Ogden, Jr.

(57) ABSTRACT

The present invention relates to a bar soap composition that contains zinc pyrithione (ZPT) and a metal-pyridine oxide complex, preferably a zinc-pyridine oxide complex. The bar soap may be characterized by enhanced discoloration resistance, extended shelf life, and/or increased anti-microbial efficacy.

17 Claims, 1 Drawing Sheet

(51) Int. Cl.
*A61K 8/27* (2006.01)
*A61K 8/49* (2006.01)
*C11D 3/16* (2006.01)
*A61K 8/36* (2006.01)
*A61K 8/37* (2006.01)
*C11D 1/04* (2006.01)

(56) References Cited

U.S. PATENT DOCUMENTS

| | | | |
|---|---|---|---|
| 3,281,366 A | 10/1966 | Judge et al. | |
| 3,412,033 A | 11/1968 | Karsten | |
| 3,725,547 A | 4/1973 | Kooistra | |
| 4,161,526 A | 7/1979 | Gorman | |
| 4,205,062 A | 5/1980 | Daahn | |
| 4,345,080 A | 8/1982 | Bolich, Jr. | |
| 4,379,753 A | 4/1983 | Bolich, Jr. | |
| 4,482,715 A | 11/1984 | Trotz et al. | |
| 4,533,736 A | 8/1985 | Trotz | |
| 4,565,693 A | 1/1986 | Marschner | |
| 4,708,863 A | 11/1987 | Bews et al. | |
| 4,714,563 A | 12/1987 | Kajs | |
| 4,818,436 A | 4/1989 | French et al. | |
| 4,935,061 A | 6/1990 | French | |
| 4,957,658 A | 9/1990 | French et al. | |
| 5,037,818 A | 8/1991 | Sime | |
| 5,104,645 A | 4/1992 | Cardin et al. | |
| 5,198,140 A | 3/1993 | Joshi | |
| 5,540,860 A | 7/1996 | Hosseini et al. | |
| 5,562,995 A | 10/1996 | Kappock | |
| 5,573,699 A | 11/1996 | Jones et al. | |
| 5,612,301 A | 3/1997 | Inman | |
| 5,714,447 A | 2/1998 | Jones | |
| 5,883,154 A | 3/1999 | Kappock | |
| 5,886,031 A | 3/1999 | Shin et al. | |
| 5,972,920 A | 10/1999 | Seidel | |
| 6,015,547 A | 1/2000 | Yam | |
| 6,017,562 A | 1/2000 | Kaufman et al. | |
| 6,017,936 A | 1/2000 | Polson et al. | |
| 6,096,122 A | 8/2000 | Kappock | |
| 6,096,297 A | 8/2000 | Jones et al. | |
| 6,162,446 A * | 12/2000 | Hani et al. | 424/401 |
| 6,242,007 B1 | 6/2001 | Mohseni et al. | |
| 6,277,360 B1 | 8/2001 | Carew et al. | |
| 6,432,432 B1 | 8/2002 | Mohseni et al. | |
| 6,451,300 B1 | 9/2002 | Dunlop et al. | |
| 6,465,015 B1 | 10/2002 | Mohseni et al. | |
| 6,649,155 B1 | 11/2003 | Dunlop et al. | |
| 6,673,756 B2 | 1/2004 | Sonnenberg et al. | |
| 6,682,724 B2 | 1/2004 | Mohseni et al. | |
| 6,887,859 B2 | 5/2005 | Clapp et al. | |
| 6,974,569 B2 | 12/2005 | Dunlop et al. | |
| 7,026,308 B1 | 4/2006 | Gavin et al. | |
| 7,381,415 B2 | 6/2008 | Yokoyama et al. | |
| 7,544,367 B2 | 6/2009 | Mohseni et al. | |
| 7,553,481 B2 | 6/2009 | Kozasa et al. | |
| 7,674,785 B2 | 3/2010 | Gavin et al. | |
| 8,119,168 B2 | 2/2012 | Johnson et al. | |
| 8,491,877 B2 | 7/2013 | Schwartz et al. | |
| 2002/0001605 A1 | 1/2002 | Carew | |
| 2004/0058855 A1 | 3/2004 | Schwartz | |
| 2004/0161435 A1 | 8/2004 | Gupta | |
| 2004/0186030 A1 | 9/2004 | Hofrichter | |
| 2004/0191331 A1 | 9/2004 | Schwartz et al. | |
| 2004/0213751 A1 | 10/2004 | Schwartz et al. | |
| 2005/0118276 A1 | 6/2005 | Lei et al. | |
| 2005/0244352 A1 | 11/2005 | Lemoine et al. | |
| 2006/0111259 A1 * | 5/2006 | Chakrabarty et al. | 510/141 |
| 2006/0171911 A1 | 8/2006 | Schwartz et al. | |
| 2007/0009463 A1 | 1/2007 | Niebauer et al. | |
| 2007/0128147 A1 | 6/2007 | Schwartz et al. | |
| 2007/0190177 A1 | 8/2007 | Kling et al. | |
| 2008/0063618 A1 | 3/2008 | Johnson et al. | |
| 2008/0138442 A1 | 6/2008 | Johnson et al. | |
| 2008/0160093 A1 | 7/2008 | Schwartz et al. | |
| 2008/0206355 A1 | 8/2008 | Schwartz et al. | |
| 2008/0249136 A1 | 10/2008 | Annis et al. | |
| 2011/0039469 A1 | 2/2011 | Cabell et al. | |
| 2011/0197906 A1 | 8/2011 | Schwartz | |
| 2011/0197907 A1 | 8/2011 | Schwartz | |
| 2011/0200649 A1 | 8/2011 | Schwartz | |
| 2011/0200650 A1 | 8/2011 | Schwartz | |
| 2011/0201588 A1 | 8/2011 | Schwartz | |
| 2012/0039966 A1 | 2/2012 | Capretta et al. | |
| 2012/0103151 A1 | 5/2012 | Jones et al. | |
| 2012/0216408 A1 | 8/2012 | Cook et al. | |
| 2012/0219610 A1 | 8/2012 | Smith, III et al. | |
| 2012/0220516 A1 | 8/2012 | Smith et al. | |
| 2012/0246851 A1 | 10/2012 | Smith, III et al. | |
| 2012/0324736 A1 | 12/2012 | Eagleton | |
| 2013/0042482 A1 | 2/2013 | Bradford et al. | |
| 2013/0045248 A1 | 2/2013 | Coffindaffer et al. | |
| 2013/0045255 A1 | 2/2013 | Smith, III et al. | |
| 2013/0045256 A1 | 2/2013 | Schwartz | |
| 2013/0045257 A1 | 2/2013 | Alwattari et al. | |
| 2013/0045263 A1 | 2/2013 | Smith, III et al. | |
| 2013/0045284 A1 | 2/2013 | Stella | |
| 2013/0045907 A1 | 2/2013 | Lanzalaco et al. | |
| 2013/0045961 A1 | 2/2013 | Smith, III et al. | |
| 2013/0048005 A1 | 2/2013 | Smith, III et al. | |
| 2013/0205959 A1 | 8/2013 | Jones et al. | |
| 2013/0222057 A1 | 8/2013 | Henshaw | |
| 2013/0280200 A1 | 10/2013 | Schwartz | |

FOREIGN PATENT DOCUMENTS

| | | | |
|---|---|---|---|
| EP | 0158481 A2 | 10/1985 | |
| EP | 0196824 A2 | 10/1986 | |
| EP | 0217635 A2 | 4/1987 | |
| EP | 0285388 A2 | 10/1988 | |
| EP | 0468564 A2 | 1/1992 | |
| GB | 2 342 862 A | 4/2000 | |
| JP | 2001-278863 A | 10/2001 | |
| JP | 2006-176675 | 12/2004 | |
| WO | 94/14408 A1 | 7/1994 | |
| WO | 94/14409 A1 | 7/1994 | |
| WO | 99/66886 A1 | 12/1999 | |
| WO | 00/35413 A1 | 6/2000 | |
| WO | WO 01/47481 A1 | 7/2001 | |
| WO | 02/00178 A1 | 1/2002 | |
| WO | 2006/110386 A1 | 10/2006 | |
| WO | 2011/147941 A1 | 12/2011 | |
| WO | 2012/058557 A2 | 5/2012 | |
| WO | 2012/116466 A1 | 9/2012 | |

OTHER PUBLICATIONS

"The stability of 2-pyridinethiol-1-oxide, sodium salt, as a function of pH", Robert J. Fenn et al, J. Soc. Cosmet. Chem., 33, 243-248 (Aug. 1982).

"Effect of Premicellar Aggregation on the pKa of Fatty Acid Soap Solutions", J.R. Kanicky et al., Langmuir 2003, 19, 2034-2038, 2003 American Chemical Society, Published on Web Feb. 7, 2003.

"Chromatographic Behavior of Pyrithiones", Caren Anja Doose et al., Journal of Chromatography A, 1052 (2004) 103-110.

"Effect of Degree, Type, and Position of Unsaturation on the pKa of Long-Chain Fatty Acids", James R. Kanicky et al, Journal of Colloid and Interface Science 256, 201-207 (2002).

PCT International Search Report and Written Opinion for PCT/US2012/026880, dated May 29, 2012.

PCT International Search Report and Written Opinion for PCT/CN2014/072729, dated May 28, 2014.

International Search Report PCT/CN2014/072565 mailed Jun. 11, 2014 including the Written Opinion of the International Searching Authority, 12 pages.

Dandruff-free Shampoo for Men, Database GNPD, Mintel, Jul. 2009, Record ID: 1146035.

International Preliminary Report on Patentability and Written Opinion of the International Searching Authority, PCT/CN2014/072565, mailed Sep. 24, 2015, 6 pages.

International Preliminary Report on Patentability and Written Opinion of the International Searching Authority, PCT/CN2013/072648 mailed Sep. 24, 2015, 5 pages.

(56) References Cited

OTHER PUBLICATIONS

Roques et al., In vitro antifungal efficacy of ciclopirox olamine alone and associated with zinc pyrithione compared to ketoconazole against Malassezia globosa and Malassezia restricta reference strains, Mycopathologia, vol. 162, No. 6, Dec. 2006, pp. 395-400.

Schmidt-Rose et al., Efficacy of a piroctone olamine/climbazol shampoo in comparison with a zinc pyrithione shampoo in subjects with moderate to severe dandruff, International Journal of Cosmetic Science, vol. 33, No. 3, Jun. 2011, pp. 276-282.

Supplementary International Search Report, PCT/CN2014/072565, mailed Jul. 22, 2015, 7 pages.

\* cited by examiner

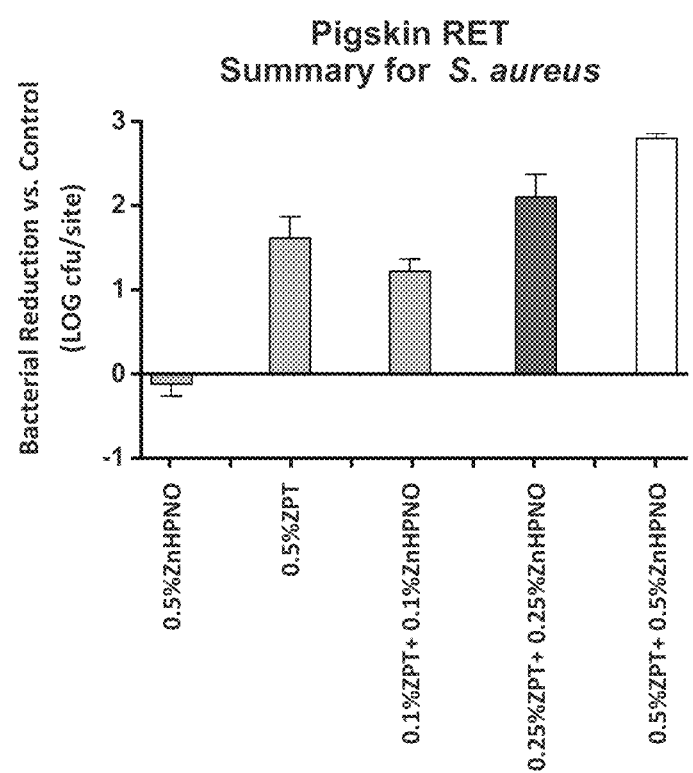

US 9,333,157 B2

BAR SOAP COMPOSITIONS CONTAINING ZINC PYRITHIONE AND A METAL-PYRIDINE OXIDE COMPLEX

FIELD OF THE INVENTION

The present invention relates to personal cleansing compositions, more specifically bar soap compositions, comprising zinc pyrithione and a metal-pyridine oxide complex with enhanced discoloration resistance, extended shelf life, and/or increased anti-microbial efficacy.

BACKGROUND OF THE INVENTION

Pyrithione (also known as 1-Hydroxy-2-pyridinethione, 2-pyridinethiol-1-oxide, 2-mercaptopyridine-N-oxide, pyridine-2-thione-N-oxide, pyridinethione-N-oxide, 2-pyridinethione, pyridinethione, or simply "PT") has been noted for its bactericidal and fungicidal activities. Pyrithione is a bidentate ligand that forms stable complexes with most transitional metals. Metallization of pyrithione often results in highly augmented biocidial activities. Metal salts of pyrithione, such as for example, sodium pyrithione, magnesium pyrithione, barium pyrithione, bismuth pyrithione, strontium pyrithione, copper pyrithione, zinc pyrithione, cadmium pyrithione, and zirconium pyrithione, are widely used as fungicides and bactericides in a broad spectrum of commercial products, such as metalworking fluids, lubricants, paints, cosmetics and toiletries.

Zinc pyrithione (or "ZPT") is especially useful as a broad-spectrum anti-microbial agent and preservative. It is active against both gram-positive and gram-negative bacteria, as well as fungi and yeasts. Therefore, ZPT has been used in various personal care compositions, such as for example, anti-dandruff shampoos, hair conditioners, leave-on tonics, and anti-microbial foot powders.

Bar soap is a popular product form for cleansing. A bar soap comprising ZPT is particularly desirable for its broad-spectrum anti-microbial efficacy. Aesthetics of consumer products such as bar soaps have significant impact on the consumers' perception of the products, which will in turn determine the acceptability of the products by the consumers. However, pyrithione-containing compounds can become discolored in the presence of ferric or cupric ions, even if the ferric irons are present only in trace amounts. The metal ions can also be introduced into the soap compositions unintentionally as impurities in the raw materials used for making bar soap. Further, during manufacturing, handling or storage, various metallic parts of the manufacturing equipment, such as for example, roller mills, pipes, or nozzles, may come into contact with the soap noodles or pellets, thereby introducing metal ions into the soap composition. In some situation, such contact can be maintained for a long time (e.g. overnight to 24 hours), and at a relatively elevated temperature, thereby increasing interaction between ZPT and metal ions. The resultant discoloration may adversely affect the overall aesthetics of the bar soaps and give consumers a negative impression of the soap quality.

In the past, a number of solutions have been developed in attempt to solve the ZPT discoloration problem. For example, in U.S. Pat. No. 4,161,526, JP Patent Publication 2001-278863A, U.S. Pat. No. 4,482,715, U.S. Pat. No. 4,957,658 and U.S. Pat. No. 4,818,436, a number of materials including zinc-containing materials, borates, reducing agents (such as alkali metal sulfites, alkali metal bisulfites, hydrazine and the like), and HEDP have been used to address the ZPT discoloration problem. However, none of these solutions can completely eliminate or effectively reduce the undesirable discoloration in ZPT-containing bar soaps, which remains a continuing concern for manufacturers.

There is a continuing need for improved ZPT-based anti-microbial bar soaps with better color stability or enhanced resistance against development of discoloration.

Further, ZPT has been known to be unstable when solubilized. It may undergo transformation upon exposure to oxidizing species or certain transition metals, such as copper and iron. The anti-microbial effect of ZPT-based personal care compositions can therefore diminish substantially over time in environments susceptible to oxidation or metallization.

Therefore, there is also a need for ZPT-based anti-microbial personal cleansing compositions with improved and extended shelf life or enhanced anti-microbial efficacy.

SUMMARY OF THE INVENTION

The present invention relates to a personal cleansing composition containing: (a) ZPT, (b) particles of a metal-pyridine oxide complex, which comprises a pyridine oxide compound coordinately bound to metal ions, and (c) at least one surfactant. Such a personal cleansing composition is preferably in the form of a bar soap and characterized by a pH value ranging from about 10 to about 10.7 when dispersed in a 1 wt % aqueous solution In another aspect, the present invention relates to a method for forming a bar soap, which includes the steps of: (a) preparing a mixture containing about 0.01% to about 5% of ZPT, from about 0.01% to about 10% of particles of the above-described metal-pyridine oxide complex, and from about 20% to about 95% of at least one surfactant by total weight of said mixture; and (b) shaping the mixture to form a bar soap. The bar soap so formed preferably has a pH value ranging from about 10 to about 10.7 when dispersed in a 1 wt % aqueous solution.

In an embodiment, the metal in the metal-pyridine oxide complex may be selected from the group consisting of iron, copper and zinc. In a preferred but non-limiting embodiment of the present invention, the particles of Zn-pyridine oxide complex are pre-formed by combining a pyridine oxide compound with zinc oxide or a soluble zinc salt and then mixed with ZPT and the surfactant. In an alternative embodiment, such particles of Zn-pyridine oxide complex are formed in situ by directly combining the pyridine oxide compound, zinc oxide or a soluble zinc salt, ZPT and the surfactant.

These and other aspects of the present invention will become more apparent upon reading the following drawings and detailed description of the invention.

BRIEF DESCRIPTION OF THE DRAWING

FIG. 1 is a graph showing the bacteria reduction rates of various soap compositions that respectively contain 0.5% ZPT alone, 0.5% Zn-HPNO complex alone, and combinations of ZPT and Zn-HPNO complex at various concentrations (e.g., 0.1%, 0.25% and 0.5%) against a gram-positive bacteria, *Staphylococcus aureus* (*S. aureus*), as measured by the pigskin Residual Efficacy Test (RET) test.

DETAILED DESCRIPTION OF THE INVENTION

"Bar soaps" as used herein refers to solid or semi-solid articles for washing, bathing, and cleaning that contain either soap surfactants, synthetic surfactants, or mixtures thereof (i.e., semi-synthetics) as described hereinafter. A bar soap as used herein is not limited to a bar shape but can have any regular or irregular shape, including but not limited to: cubic, rectangular, spherical, oval, cylindrical, pyramidal and the like. The bar soaps of the present invention are preferably, but not necessarily, characterized by a volume ranging from 1 cm$^3$ to 1,000 cm$^3$, more preferably from 10 cm$^3$ to 500 cm$^3$, and most preferably from 50 cm$^3$ to 200 cm$^3$, and a weight ranging from 0.5 g to 5 Kg, more preferably from 1 g to 1 Kg, and most preferably from 10 g to 500 g.

Except as otherwise noted, the articles "a", "an", and "the" mean "one or more." The term "comprising" means that other steps and other ingredients which do not affect the end result can be added, and this term encompasses the terms "consisting of" and "consisting essentially of". The compositions and methods/processes of the present invention can comprise, consist of, and consist essentially of the essential elements and limitations of the invention described herein, as well as any of the additional or optional ingredients, components, steps, or limitations described herein. Particularly, the compositions of the present invention contain ZPT, at least one acidic pH adjusting agent, and at least one soap surfactant as the essential ingredients, and they may contain one or more additional or optional ingredients as described hereinafter.

All percentages, parts and ratios are based upon the total weight of the personal cleansing compositions of the present invention, unless otherwise specified. All such weights as they pertain to listed ingredients are based on the active level and, therefore do not include carriers or by-products that may be included in commercially available materials.

All ratios are weight ratios unless specifically stated otherwise. All temperatures are in Celsius degrees, unless specifically stated otherwise.

As used herein, the term "effective" means an amount of a subject active high enough to provide a significantly positive modification of the condition to be treated. An effective amount of the subject active will vary with the particular condition being treated, the severity of the condition, the duration of the treatment, the nature of concurrent treatment, and like factors.

In one aspect, the present invention relates to a bar soap composition comprising the combination of ZPT and particles of a metal-pyridine oxide complex and has an overall pH value ranging from 9.9 to 10.7 when dispersed in a 1 wt % aqueous solution. Such a bar soap composition exhibits enhanced color stability or discoloration resistance, particularly in the presence of high concentration of ferric or cupric ions.

In an embodiment, the metal in the metal-pyridine oxide complex is selected from the group consisting of iron, copper and zinc. However, it will be understood by one skilled in the art that other metals can be selected according to the Irving Williams Series. Without wishing to be bound by any particular theory, it is believed that the presence of particles of a Zn-pyridine oxide complex in a bar soap composition of pH 9.9 to 10.7 is particularly effective in inhibiting or retarding transchelation between dissolved pyrithione (PT) ions and ferric or cupric ions and formation of colored precipitates, thereby eliminating or significantly reducing discoloration. In addition, the existence of such a Zn-pyridine oxide complex leads to a visible change of color in any precipitate actually formed, i.e., from a black/blue/green hue to a more visually acceptable red/orange hue. Such red/orange hue is unlikely to have adverse impact on the consumer's acceptability of the bar soap product.

Further, bar soap compositions containing the combination of ZPT and Zn-pyridine oxide complex within the scope of the present invention exhibit substantially extended shelf life by stabilizing ZPT against potential environmental assaults. This technical effect is both surprising and unexpected, especially in light of the fact that addition of uncomplexed pyridine oxide compound into the bar soap compositions containing ZPT not only fails to stabilize ZPT but in fact attributes to its further deterioration.

Still further, the combination of ZPT with Zn-pyridine oxide complex results in a synergistic enhancement of anti-microbial efficacy against gram-positive bacteria, such as *Staphylococcus aureus* (*S. aureus*).

Although bar soap is the preferred product form for carrying the combination of ZPT and Zn-pyridine oxide complex, the scope of the present invention is not thus limited. Instead, the present invention may also encompass other product forms of rinse-off personal cleansing compositions, which include but are not limited to: body washes, shower gels, liquid hand soaps, shampoos, conditioners, facial cleansers, and the like.

Zinc Pyrithione (ZPT)

Zinc pyrithione (ZPT) is incorporated in the personal cleansing compositions of the present invention in the form of a combination, a mixture, a dispersion, a suspension, or an emulsion. Preferably, but not necessarily, ZPT is present in a spherical or platelet form, while the ZPT particles have an average size of up to about 20 microns, more preferably up to about 10 microns, even more preferably up to about 5 microns, and most preferably up to about 2.5 microns. Alternatively, ZPT is present in a particulate form that is non-platelet and non-spherical, having a configuration selected from the group consisting of rods, needles, cylinders, cones, ellipsoids, prisms, parallelepipeds, pyramids, tetrahedrons, hexahedrons, octahedrons, dodecahedrons, icosahedrons, and combinations thereof, as described by U.S. Pat. No. 6,242,007.

In a preferred embodiment of the present invention, the ZPT included in the bar soap composition is a dry powder ZPT in platelet particle form ("platelet ZPT"). Such platelet ZPT can have a median particle diameter of, for example, from about 0.05 to about 10 microns, alternatively from about 0.1 to about 8 microns, and alternatively from about 0.2 to about 5 microns, and alternatively about 3 microns. The platelet ZPT can also have a thickness of, for example, from about 0.1 to about 15 microns, alternatively from about 0.5 to about 1 micron, alternatively from about 0.6 to about 0.8 microns, and alternatively from about 0.6 to about 0.7 microns, as described in U.S. Patent Publication 2012/0219610.

ZPT as used in the present invention may be made by reacting 1-hydroxy-2-pyridinethione (i.e., pyrithione acid) or a soluble salt thereof with a zinc salt (e.g., $ZnSO_4$) to form a ZPT precipitate, as illustrated by the disclosures of U.S. Pat. No. 2,809,971, or processed into platelet ZPT using, for example, sonic energy as illustrated by U.S. Pat. No. 6,682,724, or by any other methods currently known in the art. While higher concentrations of ZPT have been observed to control the growth of a wider range of micro-organisms, the useful amount of ZPT that can be added to a commercial product is limited by efficacy and economic considerations, regulatory restrictions, and environmental concerns. In personal cleansing compositions, such as soaps, the amount of ZPT that may be added is further limited by toxicological concerns. Preferably, but not necessarily, the bar soap compositions of the present invention contains ZPT in the amount ranging from about 0.01% to about 5% by total weight of such compositions. More preferably, such compositions contains from about 0.1% to about 2.0% ZPT by total weight.

Particles of Metal-Pyridine Oxide Complex

The personal cleansing compositions of the present invention further comprise a metal-pyridine oxide complex, which comprises a pyridine oxide compound that is coordinately bound to a metal ion. In an embodiment, the metal is selected from the group consisting of iron, copper and zinc. However, it will be understood by one skilled in the art that other metals can be selected according to the Irving Wiliams Series, which refers to the relative stability of complexes formed by a metal ion. In a preferred embodiment, the metal is zinc. Such zinc-pyridine oxide complex has a surprising and unexpected effect on the discoloration resistance of the ZPT-containing bar soap compositions, which is demonstrated by a significant increase in its resistance to laboratory-induced discoloration in comparison with control samples containing ZPT only. Without wishing to be bound by theory, according to Iriving Williams Series, a more stable complex can be formed between pyrithione and metal ions having smaller ionic radius. For example, $Fe^{3+}$ has a radius of 0.64 A, which is smaller than $Cu^{2+}$ which has a radius of 0.73 A, and which is in turn smaller than that of $Zn^{2+}$ 0.74 A. Thus, this might help to explain why you have pyrithione discoloration in ZPT-containing bar soaps in the presence of other transition metal sources (e.g., copper and iron).

According to this embodiment, the zinc-pyridine oxide complex acts in synergy with ZPT to improve the anti-microbial effect of the personal cleansing compositions, especially against gram-positive bacteria. It may further provide an extended shelf life for such anti-microbial personal cleansing compositions.

In a particularly preferred embodiment of the present invention, the pyridine oxide compound has the following chemical structure:

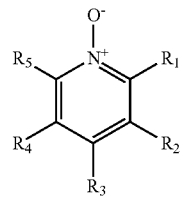

(I)

wherein $R_1$, $R_2$, $R_3$, $R_4$, and $R_5$ are each independently selected from the group consisting of H, OH, a halogen (such as F, Cl, Br, and I), NO, $NO_2$, and a $C_1$-$C_{12}$ organic group that is linear or branched, saturated or unsaturated, substituted or unsubstituted.

More preferably, $R_1$ or $R_5$ is OH, and $R_2$, $R_3$, and $R_4$ is each independently selected from the group consisting of H, OH, and a $C_1$-$C_8$ alkyl, alkylene, alkyne, or aryl group. It is to be understood that various potential and actual resonate structures of the pyridine oxides may exist (i.e., the bond between the N and O atoms and/or the bond between the neighboring C atom and —OH group may resonate between a single bond and a double bond), for example, as follows:

It is intended that all of the reasonable resonate structures are meant to be represented by the formula (I) hereinabove and are thereby included within the scope of the present invention.

Useful pyridine oxide compounds that can be employed in the practice of the present invention include 2-hydroxypyridine-N-oxide ("HPNO"), N-hydroxy-6-octyloxy-2(1H)-pyridone, ciclopirox olamine, piroctone olamine, and derivatives thereof.

A representative species of pyridine oxide compounds that is particularly useful for the practice of the present invention is 2-hydroxypyridine-N-oxide ("HPNO"), which has the chemical structure of:

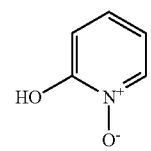

(II)

As a bidentate chelant, HPNO is capable of forming coordination complexes with transition metal ions in solution. Specifically, two HNPO can be bound to one zinc ion to form a Zn-HNPO complex with the following structure:

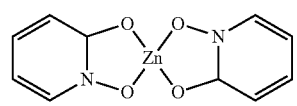

(III)

Zn-HPNO is a particularly preferred Zn-pyridine oxide compound for the present invention. It is important to note that zinc ions can form various complexes with HPNO, with one, two, three, or even four HPNO attached to one zinc ion, although only the complex with two HPNO attached to one zinc ion as shown by formula (III) has a neutral charge. In solution, zinc ions and HPNO may undergo speciation to form a mixture of different complex species, and the relative concentration of such complex species can vary depending on the chemical environment they are in, such as pH and the presence of other metal ions or chelant species. For ease of reference, all such complex species are herein referred to as the "Zn-HPNO complex," regardless of the actual number of HPNO included, and they are all included within the scope of the present invention.

Various derivatives or salts of HPNO with similar chemical structure can also form similar complexes with Zn ions and are therefore also useful for the practice of the present invention. Exemplary HPNO derivatives or salts include, but are not limited to: 6-hydroxy-3-pyridine sulfonic acid, 1-oxide (CAS 191672-18-1); 2-hydroxy-4-pyridine carboxylic acid,

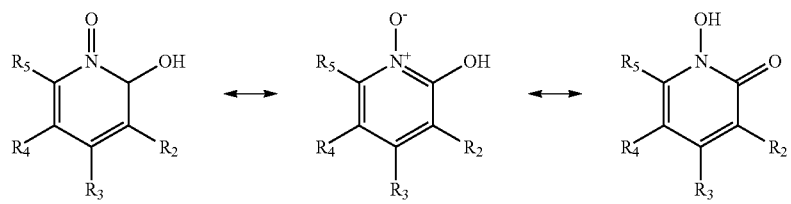

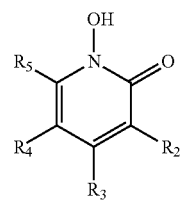

1-oxide (CAS 13602-64-7); 5-ethoxy-2-pyridinol, 2-acetate, 1-oxide (CAS 51984-49-7); 1-(3-hydroxy-2-oxido-4-isoquinolinyl)-ethanone (CAS 65417-65-4); 6-hydroxy-3-pyridine carboxylic acid, 1-oxide (CAS 90037-89-1); 2-methoxy-4-quinolinecarbonitrile, 1-oxide (CAS 379722-76-6); 2-pyridine carboxylic acid, 6-hydroxy-, 1-oxide (CAS 1094194-45-2); 3-pyridine carboxylic acid, 2-hydroxy-, 1-oxide (CAS 408538-43-2); 2-pyridinol, 3-nitro-, 1-oxide (CAS 282102-08-3); 3-pyridine propanenitrile, 2-hydroxy-, 1-oxide (193605-60-6); 3-pyridine ethanol, 2-hydroxy-, 3-acetate, 1-oxide (CAS 193605-56-0); 2-pyridinol, 4-bromo-, 1-oxide (CAS 170875-41-9); 2-pyridinol, 4,6-dibromo-, 2-acetate, 1-oxide (CAS 170875-40-8); 2-pyridinol, 4,6-dibromo, 1-oxide (CAS 170875-38-4); 2-pyridinol, 4-(2-aminoethyl)-, 1-oxide (CAS 154403-93-7); 2-pyridinol, 5-(2-aminoethyl)-, 1-oxide (CAS 154403-92-6); 3-pyridine propanoic acid, α-amino-6-hydroxy-, 1-oxide (CAS 134419-61-7); 2-pyridinol, 3,5-dimethyl, 1-oxide (CAS 102074-62-4); 2-pyridinol, 3-methyl-, 1-oxide (CAS 99969-07-0); 2-pyridinol, 3,5-dinitro, 1-oxide (CAS 98136-47-1); 2-pyridinol, 3,5-dibromo-, 1-oxide (CAS 98136-29-9); 2-pyridinol, 4-methyl-6-(2-methylpropyl)-, 1-oxide (CAS 91408-77-4); 2-pyridinol, 3-bromo-4,6-dimethyl-, 1-oxide (CAS 91408-76-3); 2-pyridinol, 4,5,6-trimethyl-, 1-oxide (CAS 91408-75-2); 2-pyridinol, 6-heptyl-4-methyl-, 1-oxide (CAS 91408-73-0); 2-pyridinol, 6-(cyclohexylmethyl)-4-methyl-, 1-oxide (CAS 91408-72-9); 2-pyridinol, 6-bromo-, 1-oxide (CAS 89284-00-4); 2-pyridinol, 5-bromo-, 1-oxide (CAS 89283-99-8); 2-pyridinol, 3,5-dichloro-4,6-difluoro-, 1-oxide (CAS 33693-37-7); 2-pyridinol, 3,4,5,6-tetrachloro-, 1-oxide (CAS 32835-63-5); 2-pyridinol, 6-methyl-, 1-oxide (CAS 14420-62-3); 2-pyridinol, 5-nitro-, 1-oxide (CAS 14396-03-3); 2-pyridinol, 4-methyl-5-nitro-, 1-oxide (CAS 13602-77-2); 2-pyridinol, 4-chloro-5-nitro-, 1-oxide (CAS 13602-73-8); 2-pyridinol, 4-chloro-, 1-oxide (CAS 13602-65-8); 2-pyridinol, 4-nitro-, 1-oxide (CAS 13602-63-6); and 2-pyridinol, 4-methyl-, 1-oxide (CAS 1952-64-3), and mixtures thereof. These compounds are commercially available from, for example, Sigma-Aldrich (St. Louis, Mo.) and/or Aces Pharma (Branford, Conn.).

The amount of zinc-pyridine oxide complex present in the bar soap compositions of the present invention may range from about 0.01% to about 10% by total weight of such compositions. More preferably, such compositions contains from about 0.05% to about 7% zinc-pyridine oxide complex, still more preferably from about 0.1% to about 7% or from about 0.5% to about 5%, or most preferably from about 1% to about 3% by total weight.

The zinc-pyridine oxide complex as used in the present invention is present in the compositions as particles, which can be pre-formed by reacting the pyridine oxide compound with a soluble zinc salt, such as $ZnSO_4$, $ZnCl_2$, or a mixture thereof, thereby forming an insoluble precipitate. The term "soluble" as used herein refers to a solubility of at least 0.01 gram per liter in an aqueous solution at 25° C. The precipitate is then processed into dry powders or used to form a colloidal or slurry composition containing particulates dispersed in a solution, which can be subsequently added into the personal cleansing compositions.

Alternatively, the particles of zinc-pyridine oxide complex can be formed in situ by directly adding the precursors, i.e., the pyridine oxide compound and the soluble zinc salt, into the personal cleansing compositions, which will complex with each other in the compositions to form particles. The pyridine oxide compound and zinc salt can be added either in dry power form or pre-dissolved in a solution.

The particles of zinc-pyridine oxide complex are characterized by an average particle size ranging from about 0.05 micron to about 5,000 microns, preferably from about 0.1 micron to about 2,000 microns, more preferably from about 0.2 micron to about 1,000 microns, and most preferably from about 1 micron to about 600 microns.

The particle size of the zinc-pyridine oxide complex can be readily controlled by modulating the homogenization rate when mixing the soluble zinc salt and the pyridine oxide compound, i.e., the faster the homogenization, the slower the particle growth rate, and consequently the smaller the particles. The particles can further be processed by milling or grinding to achieve a more uniform particle size distribution.

The molar ratio of ZPT to Zn-pyridine oxide complex in the personal cleansing compositions of the present invention is preferably ranging from about 5:1 to about 1:10, more preferably from about 2:1 to about 1:5, still more preferably from about 1:1 to about 1:3, and most preferably about 1:1.5 to about 1:2.

pH and pH Adjusting Agents

When the personal cleansing compositions of the present invention are in form of bar soaps, they are preferably characterized by a pH value ranging from 9.9 to 10.7 when dispersed in a 1 wt % aqueous solution. More preferably, the bar soap compositions have a pH range of 10.1 to 10.6, and most preferably from 10.2 to 10.5. This pH range is particularly beneficial for maintaining the dissolution equilibrium of ZPT and the Zn-pyridine oxide complex in the soap compositions, and can thereby extend or maximize the shelf life of the bar soaps.

The pH of the personal cleansing compositions of the present invention can be readily adjusted or modulated by various mechanisms. In one specific embodiment of the present invention, the pH modulation is achieved through employment of an acidic pH adjusting agent. Any acid suitable for use in personal cleansing formulation, e.g., either an inorganic acid or an organic acid, can be employed in the practice of the present invention. Examples of inorganic acid suitable for practice of the present invention include, but are not limited to: hydrochloric acid, sulfuric acid, *sulphurous* acid, nitric acid, nitrous acid, phosphoric acid, boric acid, and the like. Suitable organic acids include carboxylic acids, sulfonic acids and fatty acids.

Fatty acids are particularly preferred acidic pH adjusting agents for the practice of the present invention. Any fatty acids with total carbon numbers ranging from $C_6$ to $C_{24}$ can be used for the practice of the present invention. Exemplary fatty acids include, but are not limited to: caproic acid, caprylic acid, capric acid, lauric acid, myristic acid, palmitic acid, stearic acid, arachidic acid, behenic acid, lignoceric acid, cerotic acid, myristoleic acid, palmitoleic acid, sapienic acid, oleic acid, elaidic acid, vaccenic acid, linoleic acid, linoelaidic acid, α-linolenic acid, arachidonic acid, eicosapentaenoic acid, erucic acid, docosahexaenoic acid, and the like. Particularly useful fatty acids for the practice of the present invention are saturated or unsaturated fatty acids with total carbon numbers ranging from $C_{12}$ to $C_{22}$, such as, for example, lauric acid, myristic acid, palmitic acid, stearic acid, palmitoleic acid, oleic acid, and behenic acid.

In an alternative embodiment of the present invention, the pH modulation can be achieved by adjusting the amounts of raw materials used for soap-making, i.e., fats, oils, and base materials such as sodium or potassium hydroxide, so as to reach a final personal cleansing composition with the desired pH value. In yet another alternative embodiment of the present invention, the pH modulation can be achieved using a pH buffering agent, such as potassium carbonate or zinc carbonate.

Reducing Agents

The personal cleansing compositions of the present invention may optionally comprise one or more reducing agents, which are preferably, but not necessarily, selected from sterically hindered phenols. Such reducing agents can further improve the discoloration resistance of the soap compositions as well as extending the shelf life thereof.

Sterically hindered phenolic reducing agents suitable for the use of the present invention are characterized by a molecular weight above 500 Da. Preferred examples include 2,4-dimethyl-6-octyl-phenol; 2,6-di-t-butyl-4-methyl phenol (i.e., butylated hydroxy toluene); 2,6-di-t-butyl-4-ethyl phenol; 2,6-di-t-butyl-4-n-butyl phenol; 2,2'-methylenebis(4-methyl-6-t-butyl phenol); 2,2'-methylenebis(4-ethyl-6-t-butyl phenol); 2,4-dimethyl-6-t-butyl phenol; 4-hydroxymethyl-2,6-di-t-butyl phenol; n-octadecyl-beta(3,5-di-t-butyl-4-hydroxyphenyl)propionate; 2,6-dioctadecyl-4-methyl phenol; 2,4,6-trimethyl phenol; 2,4,6-triisopropyl phenol; 2,4,6-tri-t-butyl phenol; 2-t-butyl-4,6-dimethyl phenol; 2,6-methyl-4-didodecyl phenol; tris(3,5-di-t-butyl-4-hydroxy isocyanurate, and tris(2-methyl-4-hydroxy-5-t-butylphenyl)butane.

More preferred are pentaerythrityl tetra-di-t-butyl hydroxyhydrocinnamate (Tinoguard® TT, BASF); octadecyl-3,5-di-t-butyl-4-hydroxy-hydrocinnamate (NAUGARD 76, Uniroyal Chemical; IRGANOX 1076, Ciba-Geigy); tetrakis+methylene(3,5-di-t-butyl-4-hydroxy-hydrocinnamate)}methane (NAUGARD 10, Uniroyal Chemical; IRGANOX 1010, Ciba-Geigy); 2,2'-oxamido bis+ethyl-3-(3,5-di-t-butyl-4-hydroxyphenyl)}propionate (NAUGARD XL-1, Uniroyal Chemical); 1,2-bis (3,5-di-t-butyl-4-hydroxyhydrocinnamoyl)hydrazine (IRGANOX MD 1024, Ciba-Geigy); 1,3,5-tris(3,5-di-t-butyl-4-hydroxybenzyl)-s-tri azine-2,4,6 (1H,3H,5H)trione (IRGANOX 3114, Ciba-Geigy); 1,3,5-tris(4-t-butyl-3-hydroxy-2,6-dimethylbenzyl)-s-triazine-2,4,6-(1H,3H,5H)trione (CYANOX 1790, American Cyanamid Co.); 1,3,5-trimethyl-2,4,6-tris(3,5-di-t-butyl-4-hydroxybenzyl)benzene (ETHANOX 330, Ethyl Corp.); 3,5-di-t-butyl-4-hydroxyhydrocinnamic acid triester with 1,3,5-tris(2-hydroxyethyl)-5-triazine-2,4,6(1H,3H,5H)-trione, and bis (3,3-bis(4-hydroxy-3-t-butylphenyl)butanoic acid)glycolester.

Most preferred reducing agents for the practice of the present invention are pentaerythrityl tetra-di-t-butyl hydroxyhydrocinnamate, which is commercially available under the trade name of Tinogard® TT from BASF (Monheim, Germany).

The amount of reducing agent present in the personal cleansing compositions of the present invention may range from about 0.001% to about 5% by total weight of such compositions. More preferably, such compositions contains from about 0.01% to about 1% of the reducing agent, and most preferably from about 0.02% to about 0.5%, by total weight of such compositions.

Soap Surfactants

The bar soap of the present invention will typically comprise a soap surfactant, or in short "soap", in an amount ranging from about 40%, 45%, 50% to about 65%, 75%, 84%. The term "soap" is used herein in its popular sense, i.e., the alkali metal or alkanol ammonium salts of alkane- or alkene monocarboxylic acids. Sodium, magnesium, potassium, calcium, mono-, di- and tri-ethanol ammonium cations, or combinations thereof are suitable for purposes of the present invention. In general, sodium soaps are used in the compositions of this invention, but from about 1% to about 25% of the soap may be ammonium, potassium, magnesium, calcium or a mixture of these soaps. The soaps useful herein are the well known alkali metal salts of alkanoic or alkenoic acids having about 12 to 22 carbon atoms, preferably about 12 to about 18 carbon atoms. They may also be described as alkali metal carboxylates of alkyl or alkene hydrocarbons having about 12 to about 22 carbon atoms.

It can be preferred to use soaps having the fatty acid distribution of tallow and vegetable oil (i.e., "fatty acid soaps"). More preferably, the vegetable oil is selected from the group consisting of peanut oil, rapeseed oil, corn oil, olive oil, palm oil, coconut oil, palm kernel oil, palm oil stearine, and hydrogenated rice bran oil, or mixtures thereof, since these are among the more readily available fats. Especially preferred are palm oil stearine, palm kernel oil, and/or coconut oil. The proportion of fatty acids having at least 12 carbon atoms in coconut oil soap is about 85%. This proportion will be greater when mixtures of coconut oil and fats such as tallow, palm oil, or non-tropical nut oils or fats are used, wherein the principal chain lengths are $C_{16}$ and higher. A preferred soap is sodium soap having a mixture of about 50% tallow, 30% palm oil stearine, and 20% palm kernel oil or coconut oil.

Soaps may be made by the classic kettle boiling process or modern continuous soap manufacturing processes wherein natural fats and oils such as tallow or coconut oil or their equivalents are saponified with an alkali metal hydroxide using procedures well known to those skilled in the art. Alternatively, the soaps may be made by neutralizing fatty acids, such as lauric ($C_{12}$), myristic ($C_{14}$), palmitic ($C_{16}$), or stearic ($C_{18}$) acids with an alkali metal hydroxide or carbonate.

Synthetic Surfactants

Synthetic surfactants can be utilized in the present bar soap compositions, either in combination with or in place of the soap surfactants described hereinabove, to further improve the lathering properties of the bar soap during use. When a majority of the surfactants in the bar soap compositions of the present invention are synthetic surfactants rather than soap surfactants, the pH value of the bar soap compositions can be readily broaden to the relatively lower pH range of 7-9. In certain embodiments, the pH value of such bar soap compositions may approach the neutral pH range of 6-8, which is particularly beneficial because the resulting bar soaps are more gentle and less irritating to the skin.

The synthetic surfactants useful in this invention include anionic, amphoteric, nonionic, zwitterionic, and cationic surfactants. Synthetic surfactants are typically incorporated in the present compositions at a level of from about 0.1% to about 20%, preferably from about 0.5% to about 10%, and more preferably from about 0.75% to about 5%, by weight of the composition.

Examples of anionic surfactants include but are not limited to alkyl sulfates, anionic acyl sarcosinates, methyl acyl taurates, N-acyl glutamates, acyl isethionates, alkyl ether sulfates, alkyl sulfosuccinates, alkyl phosphate esters, ethoxylated alkyl phosphate esters, trideceth sulfates, protein condensates, mixtures of ethoxylated alkyl sulfates and the like. Alkyl chains for these surfactants are $C_8$-$C_{22}$, preferably $C_{10}$-$C_{18}$ and, more preferably, $C_{12}$-$C_{14}$ alkyls.

Zwitterionic surfactants can be exemplified by those which can be broadly described as derivatives of aliphatic quaternary ammonium, phosphonium, and sulfonium compounds, in which the aliphatic radicals can be straight chain or branched and wherein one of the aliphatic substituents contains from about 8 to 18 carbon atoms and one contains an anionic water-solubilizing group, for example, carboxy, sulfonate, sulfate, phosphate, or phosphonate. Examples include: 4-[N,N-di(2-hydroxyethyl)-N-octadecylammonio]-butane-1-carboxylate; 5-[S-3-hydroxypropyl-S-hexadecylsulfonio]-3 hydroxypentane-1-sulfate; 3-[P,P—P-diethyl-P 3,6,9 trioxatetradecyl-phosphonio]-2-hydroxypropane-1-phosphate; 3-[N,N-dipropyl-N-3-dodecoxy-2-hydroxypropylammonio]-propane-1-phosphonate; 3-(N,N-di-methyl-N-hexadecylammonio)propane-1-sulfonate; 3-(N,N-dimethyl-N-hexadecylammonio)-2-hydroxypropane-1-sulfonate; 4-(N,N-di(2-hydroxyethyl)-N-(2 hydroxydodecyl)ammonio]-butane-1-carboxylate; 3-[S-ethyl-S-(3-dodecoxy-2-hydroxypropyl)sulfonio]-propane-1-phosphate; 3-(P,P-dimethyl-P-dodecylphosphonio)-propane-1-phosphonate; and 5-[N,N-di(3-hydroxypropyl)-N-hexadecylammonio]-2-hydroxy-pentane-1-sulfate.

Examples of amphoteric surfactants which can be used in the compositions of the present invention are those which can be broadly described as derivatives of aliphatic secondary and tertiary amines in which the aliphatic radical can be straight chain or branched and wherein one of the aliphatic substituents contains from about 8 to about 18 carbon atoms and one contains an anionic water solubilizing group, e.g., carboxy, sulfonate, sulfate, phosphate, or phosphonate. Examples of compounds falling within this definition are sodium 3-dodecylaminopropionate, sodium 3-dodecylaminopropane sulfonate; N-alkyltaurines, such as the one prepared by reacting dodecylamine with sodium isethionate according to the teaching of U.S. Pat. No. 2,658,072; N-higher alkyl aspartic acids, such as those produced according to the teaching of U.S. Pat. No. 2,438,091; and the products sold under the trade name "Miranol" and described in U.S. Pat. No. 2,528,378. Other amphoterics such as betaines are also useful in the present composition. Examples of betaines useful herein include the high alkyl betaines such as coco dimethyl carboxymethyl betaine, lauryl dimethyl carboxy-methyl betaine, lauryl dimethyl alpha-carboxyethyl betaine, cetyl dimethyl carboxymethyl betaine, lauryl bis-(2-hydroxyethyl) carboxy methyl betaine, stearyl bis-(2-hydroxypropyl)carboxymethyl betaine, oleyl dimethyl gamma-carboxypropyl betaine, lauryl bis-(2-hydro-xypropyl)alpha-carboxyet-hyl betaine, etc. The sulfobetaines may be represented by coco dimethyl sulfopropyl betaine, stearyl dimethyl sulfopropyl betaine, amido betaines, amidosulfobetaines, and the like.

Examples of suitable cationic surfactants include stearyldimenthylbenzyl ammonium chloride; dodecyltrimethylammonium chloride; nonylbenzylethyldimethyl ammonium nitrate; tetradecylpyridinium bromide; laurylpyridinium chloride; cetylpyridinium chloride; laurylpyridinium chloride; laurylisoquinolium bromide; ditallow(Hydrogenated) dimethyl ammonium chloride; dilauryldimethyl ammonium chloride; and stearalkonium chloride; and other cationic surfactants known in the art.

Nonionic surfactants useful in this invention can be broadly defined as compounds produced by the condensation of alkylene oxide groups (hydrophilic in nature) with an organic hydrophobic compound, which may be aliphatic or alkyl aromatic in nature.

A preferred synthetic surfactant for use in the present compositions is sodium laureth-3 sulfate. Sodium laureth sulfate tends to provide excellent lathering properties, especially when combined with sodium tripolyphosphate as the inorganic salt in the present compositions.

Other Ingredients

The personal cleansing compositions of the present application can additionally comprise inorganic salts (especially inorganic zinc salts, such as zinc carbonate, zinc sulfate, zinc nitrate, zinc fluoride, zinc chloride, zinc borate, and the like as well as zinc oxide), structurants (such as raw starch, pregelatinzed starch, carboxymethyl cellulose, polyacrylate polymer, Carbopol, carregeenan, xanthan gum, polyethylene glycol, polyethylene oxide, and the like), free fatty acids (such as those derived from tallow, coconut, palm and palm kernel), humectants, cationic polymers (such as cationic polysaccharides, cationic polyalkylene imines, cationic hydroxyethyl cellulose, and the like), brighteners, fillers (such as silica, talc, and the like), perfumes, sequestering agents, coloring agents, opacifiers and pearlizers (such as titanium dioxide).

All of these are useful in enhancing the appearance, smell or other cosmetic/sensory properties of the product.

In a particularly preferred embodiment of the present invention, the personal cleansing compositions contain zinc carbonate at an amount ranging from about 0.01% to about 5%, more preferably from about 0.1% to about 3%, and most preferably from about 1% to about 2% by total weight of the composition Zinc carbonate provided at such an amount is particularly effective in reducing or removing malodor.

As bar soaps, the appearance of the personal cleansing compositions of the present invention can be transparent, translucent, or opaque, and the color thereof can be white, off-white, cream, yellow, pink, red, green, purple, blue and black. In one embodiment, the bar soap composition is opaque with a white or off-white color.

Preparation Methods

Bar soap compositions of the present invention can be made via a number of different processes known in the art. Preferably, the present compositions are made via a milling process, resulting in milled bar soap compositions. A typical milling process of manufacturing a bar soap composition includes: (a) a step in which the soap is made through either a continuous process (ConSap or continuous saponification process) or a batch-making process (i.e. neutralization process for hydrolysis fatty acid noodle or kettle process), (b) a vacuum drying step in which the soap is made into soap noodles, (c) an amalgamating step in which the soap noodles are combined with other ingredients of the bar soap composition, (d) a milling step in which a relatively homogeneous mixture is obtained, (e) a plodding step in which the soap mixture is extruded as soap logs and then cut into soap plugs, and (f) a stamping step in which the soap plugs are stamped to yield the finished bar soap composition. The present bar soap can be made using any of the above mentioned manufacturing processes, and the ZPT, the Zn-pyridine oxide complex (or the precursors for in situ forming such complex), and pH adjusting agent, and the reducing agent can be added during the mixing steps of preparing the bar soaps.

Other product forms of the present invention, such as body washes, shower gels, liquid hand soaps, shampoos, facial cleansers, and the like, can be readily formed by the conventional mixing or homogenization process.

Clinical Benefits

The personal cleansing compositions of the present invention have demonstrated various clinical benefits, which include but are not limited to: anti-microbial, de-germing, anti-dandruff, efficacy against atopic dermatitis, odor control, and the like.

Discoloration Test

As used herein, "discoloration" means the color change brought by formation of colored precipitates from a reaction between ZPT and unwanted metal ions, such as ferric ions and/or cupric ions. The discoloration can be in a color of grayish blue, blue, black, purple, green, and the like, which is different from the original color of a composition comprising ZPT. By "original color", it means the color of the composition before ZPT in the bar soap has an opportunity to react with ferric and/or cupric ions. For ease of measurement and comparison, discoloration in bar soaps herein is artificially induced by adding solutions containing ferric and/or cupric ions, and the color difference in the bar soaps before and after the artificial introduction of ferric and/or cupric ions is measured quantitatively using a colormeter or other well known equipment.

Specifically, once sample bar soaps are ready to be tested for discoloration resistance or the lack thereof, a circular surface area with a diameter of 23.50 mm is marked on the surface of each bar soap. Such a circular surface perfectly matches the diameter of a probe in a Gretag-Macbeth™ Color-Eye 3100 colormeter, which is employed in the present invention to measure the color LAB values of the sample bar soaps before any discoloration was induced by introduction of ferric ions ("Standard Color").

Subsequently, 60 μL of freshly prepared $FeCl_3$ solution containing 0.023 wt % of $FeCl_3$ is titrated onto the marked circular surface area to intentionally induce discoloration. After being placed under room temperature out of direct light exposure for 2 hours, various degrees of discoloration will develop on the top layer of the sample bar soap within the marked circular surface area where the $FeCl_3$ solution is titrated.

The marked circular surface area is then analyzed by the Gretag-Macbeth™ Color-Eye 3100 colormeter to determine the LAB color values of the discoloration induced by addition of the $FeCl_3$ solution ("Sample Color").

The colors are hereby quantified by the well-known LAB values. Specifically, the L value represents the lightness or brightness of the color measured, i.e., the higher the L value, the lighter or brighter the color. The A value represents the redness/greenness of the color measured, with positive A values stand for red colors and negative A values stand for green colors. The B value represents the yellowness/blueness of the color measured, with positive B values stand for yellow colors and negative B values stand for blue colors. When comparing the difference between a Sample Color and a Standard color, a positive Delta L ($\Delta L$), which is calculated as $=L_{Sample}-L_{Standard}$, indicates that the Sample Color is lighter than the Standard Color, and a negative $\Delta L$ indicates that the Sample Color is darker than the Standard Color. A positive Delta A ($\Delta A$), which is calculated as $=A_{Sample}-A_{Standard}$, indicates that the Sample Color is redder, and a negative $\Delta A$ indicates that the Sample Color is green. A positive Delta B ($\Delta B$), which is calculated as $=B_{Sample}-B_{Standard}$, indicates that the Sample Color is yellower, and a negative $\Delta B$ indicates that the Sample Color is bluer.

ZPT Stability

As mentioned hereinabove, ZPT may undergo transformation upon exposure to oxidizing species, thereby losing its anti-microbial effect over time in environments susceptible to oxidation. Such vulnerability of ZPT to environmental assaults is well known in the art, and various solutions have been proposed to stabilize ZPT with limited success.

It is a surprising and unexpected discovery of the present invention that the above-described Zn-pyridine oxide complex is effective in stabilizing ZPT in bar soap compositions and reducing ZPT loss even in harsh chemical environments.

The chemical stability of ZPT is evaluated by an aging test described as follows, so as to determine the percentage loss of ZPT after such aging test. First, a bar soap containing ZPT is obtained, preferably immediately after it is manufactured. The starting content of ZPT in such bar soap (in percentage) is measured by method described hereinafter using a portion of the bar soap, or a companion bar made from the same batch of soap noodle. The bar soap is weighed (+/−0.01 g), and its starting weight is recorded. Second, the bar soap is subjected to an aging process, during which the bar soap is placed inside a sealed water impermeable bag, which is preferably made of polyethylene (PE). The bag containing the bar soap is then left either at room temperature (i.e., about 25° C.), or in a convection oven at an elevated temperature (e.g., 50° C.), for an extended period (e.g., 10 days, 12 days, 14 days, or up to 36 months in certain cases). After the aging, if placed in a convection oven at the elevated temperature, the bar soap is taken out of the convection oven and allowed to return to room temperature (i.e., 25° C.). The bar soap is weighed again, and its final weight is recorded. The final content of ZPT in the bar soap (in percentage) is measured by the same method as described hereinafter.

Chemical stability of the ZPT is calculated by the following equation to obtain the percentage loss of ZPT:

$$\% \text{ Loss of } ZPT = \left[1 - \frac{\text{Final Bar Weight} \times \text{Final } ZPT \text{ Content } (\%)}{\text{Starting Bar Weight} \times \text{Starting } ZPT \text{ Content } (\%)}\right] \times 100\%,$$

The content of ZPT in bar soap compositions is measured herein by an iodine-based titration method, which is described in greater detail in the following sections. The mercapto group in zinc pyrithione can be titrated by iodine, which oxidizes it to the disulfide-2,2' dithiobispyridine-1-oxide. If ZPT has already been oxidized or undergone transformation otherwise so that it no longer possesses the mercapto group, it will not be detectible by the iodine-based titration method described hereinafter.

First, a standardized 0.04N iodine solution is prepared. Specifically, anhydrous sodium thiosulphate (with a minimum purity of 99%) is oven-dried for 2 hours at 105° C. and then stored in a dessicator. 0.05 grams (+/−0.0001 g) of the anhydrous sodium thiosulfate is weighed and placed into the 100 mL polypropylene beaker of an autotitrator, and 50 mL of deionized water is added to form a standard solution. The autotitrator used herein is preferably a Mettler DL25 or Mettler DM140-SC titrator with platinum ring electrode, which is commercially available from Mettler Toledo Interantional, Inc. (Switzerland), or an equivalent thereof. The autitrator is set up to titrate the standard sodium thiosulfate solution with the iodine solution that is being standardized. Bubbles are eliminated from the burette of the autotitrator, and titration is commenced. Such procedure is repeated twice more, and the results are averaged to obtain a standardized 0.04N iodine solution. The % relative standard deviation (RSD) should be less than 1% of the average.

Next, standardized 0.01N and 0.006N iodine solutions are prepared. Specifically, standardized 0.01N iodine solution is prepared using 0.10 g (+/−0.0001 g) sodium thiosulphate dissolved in 100 mL deionized water, using 10.0 mL pipetted into the 100 mL autotitrator breaker with 50 mL additional deionized water followed by the titration procedure. Standardized 0.006N iodine solution is prepared using 3.0 mL of a 0.01M sodium thiosulphate solution and 40 mL of a solvent (containing 13% v/v hydrochloric acid in 6% v/v butanol), followed by addition of 40 mL of 1:1 hexane/isopropanol.

The autotitration procedure is subsequently carried out. The iodine solutions are standardized daily.

The bar soap whose ZPT content is to be measured is then shredded using a grater and stirred to form a homogenous mixture. 4.00 grams of the shredded soap is weighed and put into a clean, dry beaker of an autotitrator. 75 mL of hot 6% v/v butanol (which was heated in a boiling-water bath) and 5 mL of concentrated HCl (provided at room temperature) are then added into the beaker. The mixture is agitated vigorously so as to fully dissolve all soluble components. The beaker is subsequently placed in the autotitrator, and bubbles are completely eliminated from the burette.

The titration is then initiated and analyzed while the mixture is still warm. The mixture is vigorously agitated during the titration procedure. For compositions with less than 0.2% of ZPT by weight, titration is carried out using the 0.006N iodine solution. For compositions with higher ZPT concentrations, the initial starting sample weight can be reduced. Titration can be done either manually or by using autotitration procedure by those with skill in the art.

The ZPT content in the bar soap is calculated as follows:

$$ZPT\ Content\ (\%) = \frac{Volume\ of\ Iodine\ Solution\ (ml) \times N \times 15.88\%}{Sample\ Weight\ (g)},$$

wherein N is the normality of the standardized iodine solution, and wherein 15.88% is a constant that is derived from:

$$15.88\% = \frac{Molecular\ Weight\ of\ ZPT \times 100\%}{Number\ of\ Pyrithione\ per\ Molecule \times 1000\ ml/Liter}$$

$$= \frac{371.6 \times 100\%}{2 \times 1000\ ml/Liter},$$

The above-described procedure is repeated three times for each bar soap composition whose ZPT content is to be measured, and the results are averaged to obtain a final ZPT content in percentage (%) for the specific bar soap. All chemical reagents employed hereinabove are high-purity reagents obtained from VWR Scientific (Batavia, Ill., USA) or other scientific chemical suppliers.

pH Measurement

The pH value of a bar soap composition is measured in aqueous solution at about 25° C., and it can be measured using any commercially available pH meter calibrated with pH standard solutions, such as, for example, the SevenMulti™ pH meter available from Mettler Toledo International, Inc. (Switzerland). Specifically, a bar soap composition whose pH value is to be measured is first dissolved in distilled water at a concentration of 1 wt % and a temperature of 35° C. by agitation provided by a magnetic stir bar in a sealed container for one hour. The soap solution is then cooled to about 25° C. (+/−0.2° C.), and the pH is measured. The pH of the 1 wt % aqueous solution is then recorded as the pH of the bar soap composition.

Water Activity

Water Activity ("Aw") is a measurement of the energy status of the water in a system. It indicates how tightly water is bound, structurally or chemically, within a composition. Water activity ("Aw") is defined as the ratio of the water vapor pressure over a sample (P) to that over pure water ($P_0$):

$$A_W = \frac{P}{P_0}$$

Water activity of a bar soap composition can be measured electronically using a water activity meter with a sealed chamber and an electrical or optical measurement of the headspace. The meter is calibrated against a series of saturated salt solutions. A bar soap composition to be measured is placed in the chamber held at ambient temperature which is then allowed to equilibrate with the headspace in the chamber. At equilibrium, the relative humidity of the air in the chamber is the same as the water activity of the composition.

For purposes of the present invention, the water activity (Aw) of a bar soap composition can be measured using a Hygrolab 3 Water Activity Meter available from Rotronic, Inc. (Huntington, N.Y., USA). The following procedure is employed to determine the water activity (Aw) of a bar soap composition:

1. Check the chamber of the meter to make sure it is clean and dry before the test;
2. Cut a bar soap into pieces of about 0.2-0.4 cm thick with a stainless steel knife;
3. Put the soap pieces into a clean, dry plastic sample container with a depth of ½";
4. Press the soap pieces with a gloved finger lightly to make sure that the bottom of the container is covered by the soap pieces;
5. Put the sample container back into the chamber of the meter and cover it with the chamber top, which contains the electronic headspace measurement apparatus;
6. Wait for the headspace to reach equilibrium (approximately 1-2 hours); and
7. Record the temperature and the Aw value.

Preferably, but not necessarily, the bar soap compositions of the present invention are characterized by a water activity of less than 0.9, more preferably between about 0.4 and 0.9, still more preferably between 0.5 and 0.9, and most preferably between 0.6 and 0.9. The bar soap can be manufactured with a water activity of about 0.85, and during distribution, such bar soap can dehydrate to obtain a lower water activity of between 0.5 and 0.8, or between 0.55 and 0.75, or between 0.6 and 0.75.

EXAMPLES

Example 1

Pre-Formation of Zinc-HPNO Complex

Particles of Zn-HPNO complex can be pre-formed using the following raw materials:

TABLE I

| Raw Materials | Nominal (w/w %) | Actual Amount (g) |
|---|---|---|
| HPNO* | 11.10 | 55.50 |
| NaOH (solid)** | 4.00 | 20.00 |
| Water 1 (DI) | 40.00 | 200.00 |
| $ZnSO_4 \cdot 7H_2O$*** | 14.35 | 71.75 |
| Water 2 (DI) | 30.55 | 152.75 |
| Total | 100.00 | 500.00 |

*Commercially available from Suzhou Highfine Biotech Co., Ltd.
**Analytical grade available from Tianjin Jiaxin Chemicals Glass Instrument Trading Co., Ltd.
***Analytical grade available from Tianjin Jiaxin Chemicals Glass Instrument Trading Co., Ltd.

The following procedure can be followed to pre-form the Zn-HNPO complex of the present invention:

Pre-weigh 200 grams of the deionized (DI) water, i.e., DI water 1;
Add 20 grams of NaOH into the DI water;
Use a magnetic bar to stir up a vortex so as to dissolve the NaOH completely;
Add 55.5 grams of HPNO into the mixture;
Use the magnetic bar to stir up a vortex so as to dissolve the HPNO until the solution turns yellowish transparent;
Pre-weigh 152.75 grams of the DI water, i.e., DI water 2, and place it in a separate container;
Add 71.75 grams of $ZnSO_4 \cdot 7H_2O$ into DI water 2;
Use a magnetic bar to stir up a vortex so as to dissolve the $ZnSO_4 \cdot 7H_2O$ completely;
Add the $ZnSO_4$ solution into the HPNO solution slowly while continuing to use the magnetic bar to stir, so as to avoid formation of any large precipitation;
Maintain the vortex by adjust the agitation speed as necessary and continue the agitation for more than 30 minutes after all the $ZnSO_4$ solution is added into the HPNO solution;
Formation Zn-HPNO precipitate in the mixture can be observed;
Let the resulting mixture sit for 1 hour;
Carefully pour out the supernatant of the mixture;
Wash the precipitant 2-3 times using DI water;
Transfer the precipitant slurry to a centrifuge tube and spin at 15,000 rpm for 30 minutes;
Pour out the supernatant again;
Transfer the resulting paste to under a ventilation hood and allow it to dry at room temperature;
The air-dried paste contains about 35% water, and the Zn-HNPO complex is 65% active therein; and
The dried powder can be further milled as necessary.

Example 2

In Situ Formation of Zinc-Pyridine Oxide Complex

A HPNO solution is first prepared by using the following raw materials:

TABLE II

| Raw Materials | Amount (w/w %) |
| --- | --- |
| HPNO | 22.20 |
| NaOH (Active, 100%) | 8.00 |
| Water (DI) | 69.80 |
| Total | 100.00 |

The following steps can be followed to form Zn-HNPO complex in situ:

Pre-weigh required amount of DI water;
Add NaOH into the DI water while gradually stirring with a magnetic bar until the mixture is transparent;
Add the required amount of HNPO into the mixture while continuing to stir with the magnetic bar until the final mixture turns transparent yellow; and
The HPNO solution and $ZnSO_4 \cdot 7H_2O$ powder are then introduced into soap noodles into amalgamator separately with other ingredients (such as perfumes, colorants, fillers, and the like) without being pre-mixed, followed by the standard soap-making processing steps such as mixing, milling, and extruding to form soap bars.

Example 3

Comparative Discoloration Test

Four different bar soaps A-D were prepared containing ingredients as listed in Table III below. Specifically, Comparative example A (i.e., the control) contained soap noodle only without any ZPT or Zn-HPNO complex. Comparative example B contained soap noodle with ZPT but without Zn-HPNO complex. Sample C contained soap noodle with ZPT in combination of pre-formed particles of Zn-HPNO complex. Sample D contained soap noodle with ZPT in combination with HPNO and ZnSO4, which reacted with each other in situ to form the Zn-HPNO complex.

TABLE III

| Ingredient (wt %) | Comparative Example A | Comparative Example B | Example C | Example D |
| --- | --- | --- | --- | --- |
| Soap Noodle* | 76.60 | 80.48 | 75.81 | 75.84 |
| ZPT | — | 0.20 | 0.20 | 0.20 |
| Pre-formed Zn-HPNO complex | — | — | 0.60 | — |
| HPNO (65% active) | — | — | — | 0.64 |
| $ZnSO_4 \cdot 7H_2O$ | — | — | — | 0.18 |
| Pentaerythrityl tetra-di-t-butyl hydroxyhydrocinnamate** | 0.00 | 0.03 | 0.03 | 0.03 |
| TiO2 | 0.40 | 0.40 | 0.40 | 0.40 |
| Starch | 17.00 | 17.00 | 17.00 | 17.00 |
| Perfume | 1.00 | 1.00 | 1.00 | 1.00 |
| Brightener-49 | 0.02 | 0.02 | 0.02 | 0.02 |
| Water | Q.S. | Q.S. | Q.S. | Q.S. |

*The soap noodle contained the following ingredients listed in Table IV.

TABLE IV

| Ingredients | Wt % |
| --- | --- |
| Sodium palmate (from palm oil and palm oil sterine) | 49.683 |
| Sodium tallowate (from tallow) | 16.027 |
| Sodium palm kernelate (from palm kernel oil) | 14.424 |
| Unsaponifiable matter | 0.540 |
| Citric acid (anhydrous) | 0.100 |
| Sodium citrate | 0.152 |

TABLE IV-continued

| Ingredients | Wt % |
| --- | --- |
| Pentasodium pentetate | 0.050 |
| Tetrasodum etidronate | 0.050 |
| Sodium chloride (low sodium) | 0.553 |
| Glycerine | 3.471 |
| Coconut acid | 0.950 |
| Water | Q.S. |

**Commercially available as Tinogard TT from BASF (Monheim, Germany).

Following are quantitative measurements of color changes in LAB values that were observed in the bar soaps before and after the addition of the $FeCl_3$ solution, following the procedure of the Discoloration Test described hereinabove:

TABLE V

| | Delta L | Delta A | Delta B |
| --- | --- | --- | --- |
| Comparative Example A | −0.462 | 0.117 | 0.542 |
| Comparative Example B | −8.377 | 2.165 | −4.653 |
| Example C | −6.5 | 0.682 | 11.298 |
| Example D | −7.257 | 1.464 | 12.87 |

The data shown in Table V hereinabove indicates that the Comparative Example A (i.e., control), which contains no ZPT, underwent very little color change before and after the addition of $FeCl_3$, while the Comparative Example B, which contained 0.2% ZPT without the Zn-HPNO complex, exhibited significant color change and more specifically, significant blue discoloration, as indicated by the negative ΔB value. In comparison, Example C and D that contained either preformed or in situ formed particles of Zn-HPNO complex exhibited highly positive ΔB values, which indicated that the color change migrated from the blue spectrum to the yellow spectrum, and that the undesirable blue discoloration was effectively eliminated by introduction of the Zn-HPNO complex.

Example 4

Comparative ZPT Stability Test

A. ZPT Only Vs. ZPT+$ZnSO_4$

A first comparative experiment was carried out to assess the percentage loss of ZPT in bar soap compositions containing ZPT alone in comparison with compositions containing ZPT in combination with $ZnSO_4$. The following two bar soap compositions were prepared:

TABLE VI

| | Amount (w/w %) | |
| --- | --- | --- |
| Raw Materials | Comparative Example E | Comparative Example F |
| Dry Soap Noodle | 76.68 | 76.68 |
| TiO2 | 0.40 | 0.40 |
| Starch | 17.00 | 17.00 |
| ZPT (48% active) | 0.42 | 0.42 |
| ZnSO4•7H2O (7.78% solution) | — | 5.00 |
| Perfume | 1.00 | 1.00 |
| Brightener 49 | 0.02 | 0.02 |
| DI water | Q.S. | Q.S. |

The pH values, initial weights and initial ZPT contents in the bar soaps of Comparative Examples E and F were measured according to the procedures described hereinabove. The bar soaps were then subjected to environment stresses in an incubator at 50° C. with 60% humidity for 12 days, after which the final weights and final ZPT contents were re-measured and used to calculate the loss of ZPT. The measurements results are as follows:

TABLE VII

| Results | Comparative Example E | Comparative Example F |
| --- | --- | --- |
| pH (1% solution) | 10.42 | 10.36 |
| Initial ZPT Content (w/w %) | 0.201 | 0.206 |
| Final ZPT Content (w/w %) | 0.199 | 0.188 |
| Initial Bar Weight (g) | 42.06 | 43.81 |
| Final Bar Weight (g) | 40.08 | 43.39 |
| ZPT Loss (%) | 5.66 | 9.61 |

The above comparative examples demonstrate that in the presence of $ZnSO_4$, ZPT in a bar soap composition is actually less stable than in that contained only ZPT.

B. ZPT Only Vs. ZPT+Zn-HNPO

A second comparative experiment was carried out to assess the percentage loss of ZPT in bar soap compositions containing ZPT alone in comparison with compositions containing ZPT in combination with Zn-HPNO complex. The following two bar soap compositions were prepared:

TABLE VIII

| | Amount (w/w %) | |
| --- | --- | --- |
| Raw Materials | Comparative Example G | Inventive Example H |
| Soap Noodle | 76.18 | 78.23 |
| TiO2 | 0.40 | 0.40 |
| Starch | 17.00 | 17.00 |
| ZPT (48% active) | 0.42 | 0.42 |
| Pre-formed Zn-HNPO particles (65% active)* | — | 0.60 |
| Perfume | 1.00 | 1.00 |
| Pentaerythrityl tetra-di-t-butyl hydroxyhydrocinnamate | 0.05 | 0.05 |
| Brightener 49 | 0.02 | 0.02 |
| DI water | Q.S. | Q.S. |

*Formed following the procedures described in Example I here in above.

The pH values, initial weights and initial ZPT contents in the bar soaps of the Comparative Example G and the Inventive Example H were measured according to the procedures described hereinabove. The bar soaps were then subjected to environment stresses in an incubator at 50° C. with 60% humidity for 12 days, after which the final weights and final ZPT contents were re-measured and used to calculate the loss of ZPT. The measurement results are as follows:

TABLE IX

| Results | Comparative Example G | Inventive Example H |
| --- | --- | --- |
| pH (1% solution) | 10.36 | 10.32 |
| Initial ZPT Content (w/w %) | 0.202 | 0.205 |
| Final ZPT Content (w/w %) | 0.192 | 0.201 |
| Initial Bar Weight (g) | 43.62 | 43.44 |
| Final Bar Weight (g) | 42.13 | 42.51 |
| ZPT Loss (%) | 8.20 | 4.05 |

The above examples demonstrated that in the presence of Zn-HPNO complex, ZPT in a bar soap composition is more stable than in that contained only ZPT.

C. ZPT+HNPO Vs. ZPT+Zn-HPNO

A third comparative experiment was carried out to assess the percentage loss of ZPT in bar soap compositions containing ZPT in combination with uncomplexed HPNO as compared with compositions containing ZPT in combination with Zn-HPNO complex. The following two bar soap compositions were prepared:

TABLE X

| | Amount (w/w %) | |
|---|---|---|
| Raw Materials | Comparative Example I | Inventive Example J |
| Soap Noodle | 98.10 | 98.10 |
| ZPT (48% active) | 0.42 | 0.42 |
| Zn-HNPO premix (HPNO concentration = 20.2%) | 0.00 | 1.48 |

TABLE X-continued

| | Amount (w/w %) | |
|---|---|---|
| Raw Materials | Comparative Example I | Inventive Example J |
| HPNO Solution (20.2% active) | 1.48 | 0.00 |
| Perfume | 1.00 | 1.00 |
| Process Moisture loss | 1.00 | 1.00 |

The Zn-HPNO premix was prepared by mixing a HPNO solution with a $ZnCl_2$ solution in the experiment, with a HPNO concentration of 20.2% and a $ZnCl_2$ concentration of 12.74%. The preparation procedures followed procedures as described hereinabove except without centrifugation. The mixture was continuously stirred to make sure that it was homogenous before addition into the soap noodle.

ZPT contents of the Comparative Example I and the Inventive Example J were measured according to the procedures described hereinabove. The bar soaps were then subjected to environment stresses in an incubator at 50° C. with 60% humidity and ambient condition for 12 days, after which final ZPT contents were measured. The measurement results are as follows:

TABLE XI

| Results | ZPT (w/w %) Ambient storage 12 days | ZPT (w/w %) 50° C./60% humidity 12 days |
|---|---|---|
| Comparative Example I | 0.20 (+/−0.01) | 0.15 (+/−0.01) |
| Inventive Example J | 0.20 (+/−0.01) | 0.20 (+/−0.01) |

The above examples demonstrated that ZPT in a bar soap composition containing uncomplexed HNPO is less stable than in that contained ZPT and Zn-HNPO complex.

Example 5

Synergistic Anti-Microbial Activity

Five different bar soap samples 1-5 were prepared containing ingredients as listed in Table V below. Specifically, Example 1 contained 0.5 wt % Zn-HPNO complex. Example 2 contained 0.5 wt % ZPT. Example 3 contained 0.1 wt % ZPT with 0.1 wt % Zn-HPNO complex. Example 4 contained 0.25 wt % ZPT with 0.25 wt % Zn-HPNO. Example 5 contained 0.5 wt % ZPT with 0.5 wt % Zn-HPNO.

TABLE XII

| Ingredients (wt %) | Comparative Example 1 | Comparative Example 2 | Inventive Example 3 | Inventive Example 4 | Inventive Example 5 |
|---|---|---|---|---|---|
| Soap Noodle* | 78.40 | 79.00 | 79.13 | 78.87 | 77.36 |
| ZPT (48%) | — | 1.04 | 0.21 | 0.52 | 1.04 |
| Zn-HPNO complex* (active 55%) | 0.91 | — | 0.18 | 0.46 | 0.91 |
| TiO2 | 0.50 | 0.50 | 0.50 | 0.50 | 0.50 |
| Brightner 49 | 0.02 | 0.02 | 0.02 | 0.02 | 0.02 |
| Starch | 17.00 | 17.00 | 17.00 | 17.00 | 17.00 |
| Perfume | 1.00 | 1.00 | 1.00 | 1.00 | 1.00 |
| Pentaerythrityl tetra-di-t-butyl hydroxyhydrocinnamate | 0.03 | 0.03 | 0.03 | 0.03 | 0.03 |
| DI Water | Q.S. | Q.S. | Q.S. | Q.S. | Q.S. |

*Same as that described in Table IV.

The pigskin Residual Efficacy Test (RET) test was conducted for the Comparative Examples 1-2 and the Inventive Examples 3-5, as follows:

First, pigskins were obtained from a local source. Pig hides were shaved, washed with soap, rinsed, cut into usable pieces, and then sterilized by irradiation. Sterilized pigskin pieces were stored at −80° C. until used.

An overnight bacterial culture of *S. aureus* (ATCC #27217) was prepared on the day prior to performing the pigskin RET method. Specifically, one bacteria colony of *S. aureus* (ATCC #27217) from a streak plate was used to inoculate into a vented flask containing 50 mL of Tryptic Soy Broth (TSB) and incubated at 33° C. for 18±2 hr with shaking at 200 rpm. On the day of the study, the overnight culture was diluted 1:20 in TSB, and 10 µL ($10^6$-$10^7$ cfu) of the diluted culture was used for inoculating pigskin slices that had already been washed by the bar soaps as described above.

Frozen pigskins were thawed to room temperature for 60-90 minutes, and then cut into 5×10 $cm^2$ pieces for bar soap washing. Pigskin pieces were affixed to a solid support using clamps to hold the skin into a fixed position, then rinsed for 15 seconds under the tap with a water flow of 4 L/min and a temperature ranging from 31° C. to 34° C. A bar soap test sample was subsequently wetted for 5 seconds with tap water and then used to wash the pigskin directly for 15 seconds by rubbing the bar soap against the skin. Subsequently, the bar soap was put aside, and the pigskin was lathered further with a gloved hand for 45 seconds. The soap-washed pigskin was then rinsed again with tap water. The water contacted the top-middle part of the skin held in a horizontal position for 15 seconds, then dried with a sterile kimwipe by gentle touching, followed by further air-drying.

The air-dried pigskin pieces were segmented using a sterile razor blade. A 2.5×10 cm² strip from the bottom part of the pig skin furthest away from where the rinse water stream contacted the pig skin was cut away and then further segmented into 1.75×2.5 cm² slices for use in the assay. Triplicate pigskin slices were inoculated with 10 μL of the prepared 1:20 bacteria dilution stock and spread on the skin with a sterile 1 μL inoculating loop. The inoculum was $10^6$-$10^7$ cfu for each tissue slice. The inoculum was allowed to dry on the tissue slides, and the resulting tissues were incubated in a large covered petri plate for 5 hours at 33° C., 60% RH. After the 5-hr incubation, tissue slices were placed into individual sterile 250 mL wide mouth bottles containing 50 mL MLBT neutralizing buffer (Modified Letheen Broth+1% Tween-80) and vigorously agitated by shaking for 1 min Serial dilutions were then made using MLBT and surviving bacteria were plated onto MLTA (Modified Letheen Agar+1% Tween-80) and quantified using a QCount instrument (Spiral Biotech). Data was subsequently analyzed and graphed using GraphPad Prism v6.01 software (GraphPad Software Inc.).

FIG. 1 shows the bacteria reduction rates of Examples 1-5 against the gram-positive bacteria, Staphylococcus aureus (S. aureus), as measured by the above-described pigskin RET test. It is clear from that the bacterial reduction rate of Example 5, which contained both ZPT and Zn-HPNO complex at 0.5 wt %, is significantly greater than the sum of bacterial reduction rates of Examples 1 and 2, each of which contained ZPT or Zn-HPNO complex alone at the same concentration. In fact, the bacterial reduction rate of Example 4, which contained ZPT and Zn-HPNO complex at a much lower concentration of 0.25 wt %, is even greater than the sum of bacterial reduction rates of Samples 1 and 2 that contained higher concentration (i.e., 0.5 wt %) of ZPT and Zn-HPNO separately.

Therefore, a synergistic antimicrobial effect was observed for personal cleansing compositions containing the combination of ZPT and Zn-HPNO complex, especially against gram-positive bacteria, such as S. aureus.

Example 6

Fractional Inhibitory Concentration (FIC) Test

Four different test agents, which included HPNO, Zn-HPNO, Octopirox, and Zn-Octopirox, were tested in combination with ZPT using the checkerboard Fractional Inhibitory Concentration (FIC) microtitration method against the gram-positive model bacteria, S. aureus. Specifically, each test was repeated three times with HPNO and Zn-HPNO complex in combination with ZPT, while each test was performed once with Octopirox and Zn-Octopirox in combination with ZPT. The ΣFIC indices were determined and averaged (Table XIII). Definitions of the activity were applied according to The American Society of Microbiology criteria for determining drug interactions.

Specifically, a 1:1000 S. aureus (ATCC #27212) bacteria inoculum was prepared from a 50 ml culture in TSB broth which was incubated (18-24 hr, 33° C.) the night prior to each study. Stock solutions for each test material were prepared in sterile water. Using 8 well (columns) by 8 well (rows) grid on a 96-well microtitre plate, 2× stocks (100 μL) of test material #1 (HPNO, Zn-HPNO, Octipirox, or Zn-Octipirox) was added to the columns of a 96-well plate with decreasing 2-fold dilutions across the plate. The final concentration range for Zn-HPNO was 1242.5 ppm to 19.4 ppm for a total of seven dilutions. The final concentration range for HPNO was 2500 ppm to 39 ppm for a total of seven dilutions. The final concentration range for Octopirox was 760 ppm to 11.9 ppm for a total of seven dilutions. The final concentration range for Zn-Octopirox was 55000 ppm to 859 ppm for a total of seven dilutions. In each case the final ($8^{th}$) column contained none of the before mentioned materials to provide a zero material column in the first dimension on the plate. In the second dimension of the plate, 10× stocks (20 μL) of ZPT was added to the "rows" of the same 96-well plate with decreasing 2-fold dilutions down the plate. The concentration range (25 ppm to 0.39 ppm for 7 dilutions) of ZPT was tested with the final ($8^{th}$) row containing no ZPT. Finally 80 μL of the previously described 1:1000 diluted S. aureus stock was added to each well of the matrix to provide a final volume of 200 μL in each well. This matrix allows for each concentration dose of ZPT to be exposed to each concentration dose of the respective test materials in the presence to the bacteria. The test plates were then incubated 22-24 h, 33° C., after which growth (opaque wells) and no growth (clear wells) determinations of each well were determined by visualization. Based on the growth or lack of growth in dosed wells, the ΣFIC indices were calculated to determine synergism, partial synergism, indifference, or antagonism according to The American Society of Microbiology criteria for determining drug interactions. Averages of the ΣFIC indices with the Standard Error of the Mean (SEM) are shown in TABLE XIII below.

TABLE XIII

| Samples | S. aureus |
|---|---|
| ZPT + ZnHPNO | 0.27 ± 0.02 |
| ZPT + HPNO | 1.25 ± 0.38 |
| ZPT + Zn-Octopirox | 1 |
| ZPT + Octopirox | 2 |

Typically, a FIC test value of <0.5 represents a synergistic effect achieved by the combination of ZPT with the additional ingredient in reducing or removing the gram-positive bacteria S. aureus. A FIC test value of 0.5-0.99 represents an additive or partial synergy effect. A FIC test value of 1-4 indicates that no difference was observed by combining ZPT with the additional ingredient. A FIC test value of >4 represents an antagonistic effect.

Therefore, the above-provided FIC test results further confirmed the synergistic anti-microbial effect achieved by combining ZPT with a Zn-pyridine oxide compound of the present invention in reducing or removing the gram-positive bacteria S. aureus, which was not observed when an uncomplexed pyridine oxide compound (e.g., HPNO or Octopirox without Zn) was added into the solution containing ZPT.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, except WO patent application no. CN2013/072648, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A personal cleansing soap bar composition comprising:
   (a) from 0.01% to 5% by weight of zinc pyrithione (ZPT);
   (b) from 0.01% to 10% by weight of particles of a Zinc-pyridine oxide complex; and
   (c) from 20% to 95% by weight of at least one surfactant, wherein said personal cleansing composition has a pH value ranging from 9.9 to 10.7 when dispersed in a 1 wt % aqueous solution.

2. The personal cleansing composition of claim 1, comprising a Zn-pyridine oxide complex which comprises a pyridine oxide compound that is coordinately bound to zinc ions, and wherein the pyridine oxide compound is selected from the group consisting of 2-hydroxypyridine-N-oxide (HPNO), N-hydroxy-6-octyloxy-2(1H)-pyridone, ciclopirox olamine, piroctone olamine, and derivatives and combinations thereof.

3. The personal cleansing composition of claim 2, wherein the molar ratio of ZPT to the Zn-pyridine oxide complex ranges from 5:1 to 1:10.

4. The personal cleansing composition of claim 1, further comprising a reducing agent.

5. The personal cleansing composition of claim 4, wherein the reducing agent is a sterically hindered phenol.

6. The personal cleansing composition of claim 4, wherein the reducing agent is pentaerythrityl tetra-di-t-butyl hydroxyhydrocinnamate.

7. The personal cleansing composition of claim 2, wherein the Zn-pyridine oxide complex comprises 2-hydroxypyridine-N-oxide (HPNO) coordinately bound to zinc ions, wherein the molar ratio of ZPT to the Zn-pyridine oxide complex ranges from 5:1 to 1:10, wherein the composition further comprises a reducing agent that is pentaerythrityl tetra-di-t-butyl hydroxyhydrocinnamate.

8. The personal cleansing composition of claim 1, wherein the surfactant comprises:
   (a) from 0% to 95% fatty acid soap;
   (b) from 0% to 50% synthetic surfactant; or
   (c) mixtures thereof.

9. A bar soap comprising from 0.01% to 5% of ZPT, from 0.01% to 10% of particles of a Zn-pyridine oxide complex, and from 20% to 95% of at least one synthetic surfactant by total weight of the bar soap.

10. A method for forming a bar soap, comprising the steps of:
    (a) forming a mixture that comprises from 0.01% to 5% of ZPT, from 0.01% to 10% of particles of a Zn-pyridine oxide complex, and from 20% to 95% of at least one surfactant by total weight of the mixture; and
    (b) shaping the mixture to form a bar soap.

11. The method of claim 10, wherein the bar soap has a pH value ranging from 9.9 to 10.7 when dispersed in a 1 wt % aqueous solution.

12. The method of claim 10, wherein the Zn-pyridine oxide complex comprises a pyridine oxide compound that is coordinately bound to zinc ions, and wherein said pyridine oxide compound is selected from the group consisting of 2-hydroxypyridine-N-oxide (HPNO), N-hydroxy-6-octyloxy-2(1H)-pyridone, ciclopirox olamine, piroctone olamine, and derivatives and combinations thereof.

13. The method of claim 10, wherein the molar ratio of ZPT to the Zn-pyridine oxide complex ranges from 5:1 to 1:10.

14. The method of claim 10, wherein the particles of Zn-pyridine oxide complex are pre-formed by combining a pyridine oxide compound with zinc oxide or a soluble zinc salt and then mixed with ZPT and the surfactant.

15. The method of claim 10, wherein the particles of Zn-pyridine oxide complex are formed in situ by directly combining a pyridine oxide compound, a zinc source selected from zinc oxide or a soluble zinc salt, ZPT and the surfactant.

16. The method of claim 10, wherein the mixture further comprises a reducing agent comprising a sterically hindered phenol.

17. The method of claim 10, wherein the mixture further comprises pentaerythrityl tetra-di-t-butyl hydroxyhydrocinnamate in the amount ranging from 0.001% to 5% by total weight of the mixture.

* * * * *